United States Patent [19]
Pirrung et al.

[11] Patent Number: 5,908,926
[45] Date of Patent: Jun. 1, 1999

[54] 5' TO 3' NUCLEIC ACID SYNTHESIS USING 3'-PHOTOREMOVABLE PROTECTING GROUP

[75] Inventors: Michael C. Pirrung, Houston, Tex.; Steven W. Shuey; Jean-Claude Bradley, both of Durham, N.C.

[73] Assignee: Duke University, Durham, N.C.

[21] Appl. No.: 08/406,327

[22] Filed: Mar. 16, 1995

[51] Int. Cl.$^6$ .............................. C07H 1/02; C07H 1/00
[52] U.S. Cl. .................................. 536/25.34; 536/25.33
[58] Field of Search ............................... 536/25.33, 25.34

[56] References Cited

U.S. PATENT DOCUMENTS

| | | | |
|---|---|---|---|
| 4,415,732 | 11/1983 | Caruthers et al. | 536/25.31 |
| 5,143,854 | 9/1992 | Pirrung et al. | 436/518 |
| 5,242,974 | 9/1993 | Holmes | 525/54.11 |
| 5,486,633 | 1/1996 | Pirrung et al. | 556/410 |
| 5,489,678 | 2/1996 | Fodor et al. | 536/22.1 |

FOREIGN PATENT DOCUMENTS

| | | |
|---|---|---|
| WO 92/10587 | 6/1992 | WIPO . |
| WO 92/10588 | 6/1992 | WIPO . |

OTHER PUBLICATIONS

Pirrung et al, "Alcohols. Asymmetric Synthesis of Phosphotriesters of (–)-3',5'-Dimethoxybenzoin", J. Org. Chem. 59(14):3890–3897 (1994).

Pirrung and Bradley, "Comparison of Methods for Photochemical Phosphoramidite–Based DNA Synthesis", J. Org. Chem., vol. 60, 1995, pp. 6270–6276.

Pirrung and Bradley, "Dimethoxybenzion Carbonates: Photochemically–Removable Alcohol Protecting Groups Suitable for Phosphoramidite–Based DNA Synthesis", J. Org. Chem., vol. 60, 1995, pp. 1116–1117.

Fodor et al, "Multiplexed biochemical assays with biological chips", Nature 364:555–556 (1993).

Fodor et al, "Light–Directed, Spatially Addressable Parallel Chemical Synthesis", Science 251:767–773 (1991).

Horne et al, "Recognition of Mixed–Sequence Duplex DNA by Alternate–Strand Triple–Helix Formation", J. Am. Chem. Soc. 112:2435–2437 (1990).

Pirrung et al, "Photochemically–Removable Silyl Protecting Groups", J. Org. Chem. 58:6961–6963 (1993).

Lew et al, Photochemical Protodesilylation of 2–$R_3Si$–1,3–dimethoxybenzenes. Direct Observation of β–Silyl–Substituted Cyclohexadienyl Cations, J. Am. Chem. Soc. 115:11516–11520 (1993).

Givens et al, "Photochemistry of Phosphate Esters", Chem. Rev. 93(1):55–66 (1993).

*Primary Examiner*—Gary L. Kunz
*Attorney, Agent, or Firm*—Nixon & Vanderhye P.C.

[57] ABSTRACT

The present invention relates, in general, to a method of synthesizing a nucleic acid, and, in particular, to a method of effecting 5' to 3' nucleic acid synthesis. The method can be used to prepare arrays of oligomers bound to a support via their 5' end. The invention also relates to a method of effecting mutation analysis using such arrays. The invention further relates to compounds and compositions suitable for use in such methods.

20 Claims, No Drawings

5' TO 3' NUCLEIC ACID SYNTHESIS USING 3'-PHOTOREMOVABLE PROTECTING GROUP

This invention was made with Government support under Grant No. DEFG0592ER 61388 awarded by the Department of Energy. The Government has certain rights in the invention.

TECHNICAL FIELD

The present invention relates, in general, to a method of synthesizing a nucleic acid, and, in particular, to a method of effecting 5' to 3' nucleic acid synthesis. The method can be used to prepare arrays of oligomers bound to a support via their 5' end. The invention also relates to a method of effecting mutation analysis using such arrays. The invention further relates to compounds and compositions suitable for use in such methods.

BACKGROUND

Through the advances in DNA technology that occurred in the 1980's, it is now possible to map the human genome, identify all the genes it contains, and study their functions. Once all the genes are known, the analysis of how they cooperate will be possible, leading to enormous advances in the understanding of diseases. Indeed, medicine in the next century can be expected to focus increasingly on DNA. The ability to synthesize, sequence, and perceive the meaning of DNA will be an essential tool in the clinical laboratory, the drug industry, and the research laboratory.

The development of detailed genetic maps of each of the 24 chromosomes will aid in the pursuit of specific disease genes. Physical maps of the genome are an essential intermediate step to obtaining the gene itself. Libraries of overlapping cloned DNA for which the position of each gene in the chromosome is known constitute appropriate physical maps. Once genes have been localized to individual clones, they will then be sequenced. As the wild-type sequences become available, this baseline information can be used in presymptomatic diagnosis of genetically-based diseases.

Key to the success of the process described above is the availability of rapid, accurate and affordable DNA sequencing techniques. One of the most widely acclaimed methods currently proposed for DNA analysis is a microchip that can be used for sequencing-by-hybridization (SBH) (Bains et al, J. Theor. Biol. 135:303 (1988); Drmanac et al, Genomics 4:114 (1989); Khrapko et al, FEBS Lett. 256:118 (1989)). In theory, a chip bearing a complete set of n-mer oligonucleotides would permit the sequencing of DNA by duplex formation with their Watson-Crick complements in a target DNA, with the only limitations being repeats of the same sequence and runs of identical bases longer than n.

In theory, the SBH method could be applied either with the probes immobilized and the target in solution (reverse blot) or vice versa. In fact, the initial experiments toward demonstrating this technology have used both. Light-directed synthesis (U.S. Pat. No. 5,143,854; Fodor et al, Science 251:767 (1991)), however, which permits the chemistry of DNA synthesis to be conducted in parallel at thousands of locations, requires probe immobilization. The number of sequences prepared using this technology far exceeds the number of chemical reactions required. In fact, for light-directed DNA synthesis of oligomers of length "l", the number of sequences prepared is $4^l$ but the number of steps required is only 4×l.

Recently, Pease et al (Proc. Natl. Acad. Sci. USA 91:5022 (1994)) have reported the results of initial efforts in preparing DNA chips through light-directed synthesis and in using them for mock sequencing experiments. Using phosphoramidite chemistry modified by the inclusion of the MeNPOC photoremovable group, Pease and colleagues have prepared arrays of 256 octamers (4 mixed nucleotide positions flanked by two CG clamps). They find that fluorescently-labeled target DNA binds selectively to its complement within the array. Some single-base mismatches, however, show as much as 20% of the fluorescence hybridization signal of the perfect complement. This results from the fact that hybridization is dependent on the exact sequences of the probes, the hybridization conditions, and the location of the mismatches (fraying at the 5' end is common in mishybridization (Wood et al, Proc. Natl. Acad. Sci. USA 82:1585 (1985)). While mishybridization is readily manageable for targets that have only one complement within an array, it could make interpretation of the hundreds of hybridization spots that will be produced with full octamer or decamer arrays and Kb DNA targets very challenging.

A second novel method for high-throughput DNA sequencing has arisen based on reversible termination of primer extension. In accordance with this method, a DNA polymerase reaction is conducted with a primer, template, and four terminators that are conventional deoxynucleotides with a blocking group at the 3' end. No dNTPs are included. Only one blocked deoxynucleotide is incorporated based on the template/primer sequences and the fidelity of the polymerase. The identity of the incorporated terminators can then be determined by tagging them with differently-colored fluorophores. The blocking group is removed (under conditions that do not damage DNA) in order to provide free 3' end for another polymerase cycle. A reasonable strategy is the incorporation of the base specific color into the blocking group.

This method has a number of experimental pitfalls, the greatest being the reversibility of DNA polymerization in the presence of enzyme. This does not refer to the 5'→3' exonuclease activity that has been removed from many of the commercial polymerase preparations by engineering, but rather to the natural reversibility of chemical reactions. Under normal primer extension conditions, this reversal is invisible because the dNTPs that are present permit the degraded strand to be built back up. Even if there is only a small amount of reversal in each cycle, the accumulation of such errors becomes significant over the hundreds or thousands of cycles needed to sequence a template of significant length.

The present invention provides a new approach to the photochemical synthesis of nucleic acids and to the preparation of high quality arrays of oligomers that permit the rapid analysis of genes, including those wherein mutations result in disease. The invention also provides new photochemically removable protecting groups that can be used in the present approach to nucleic acid synthesis.

SUMMARY OF THE INVENTION

The present invention relates, in one embodiment, to a method of effecting 5' to 3' synthesis of a nucleic acid. The method comprises:
  i) attaching to a support a nucleoside comprising a photoremovable 3' hydroxyl protecting group, wherein the attachment is via the 5' hydroxyl of the nucleoside;
  ii) irradiating the support-bound nucleoside resulting from step (i) so that the protecting group is removed and the 3' hydroxyl group is thereby freed; and
  iii) contacting the support-bound nucleoside resulting from step (ii) with a nucleotide comprising a 5' phosphoramidite under conditions such that the 5' phosphoramidite reacts with the free 3' hydroxyl so that a dinucleotide is formed.

In another embodiment, the present invention relates to a method of effecting 5' to 3' synthesis of a nucleic acid that comprises:

i) attaching a first nucleotide to a support via a 5' hydroxyl of the nucleotide, wherein the nucleotide comprises a 3' phosphotriester, one of the esters of the 3' phosphotriester being a photoremovable group;

ii) irradiating the support-bound nucleotide resulting from step (i) so that the photoremovable group is removed and a 3' phosphodiester is thereby formed;

iii) contacting the support-bound nucleotide resulting from step (ii) with a second nucleotide comprising a 5' hydroxyl group that reacts with the 3' phosphodiester of the support-bound nucleotide resulting from step (ii) so that a dinucleotide is formed.

In a further embodiment, the present invention relates to a nucleotide comprising a phosphoramidite on the 5' hydroxyl thereof and a benzoinyl carbonate on the 3' hydroxyl thereof.

In yet another embodiment, the present invention relates to a compound of formula:

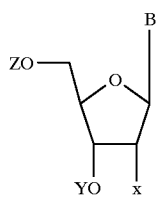

wherein: B is a nitrogenous aromatic heterocyclic group;
X is H, OH or a protected OH;
Y is a benzoinyl carbonate; and
Z is a phosphoramidite.

In still another embodiment, the present invention relates to a 3'-O-phosphoryl aryloxybenzoinyl nucleotide or 3'-O-phosphoryl cyanoethoxybenzoinyl nucleotide, or a 3'-O-phosphoryl aryloxynitrobenzyl nucleotide.

In a further embodiment, the present invention relates to an array comprising a substrate and a multiplicity of nucleotides or nucleosides attached thereto via the 5' hydroxyl group of the nucleosides or nucleotides.

DETAILED DESCRIPTION OF THE INVENTION

The present invention relates to a method of effecting 5' to 3' synthesis of a nucleic acid, for example, a nucleic acid attached to a solid support. In a preferred embodiment, the invention relates to a method of preparing arrays of nucleic acid oligomers. The oligomers are attached to the array substrate (support) through their 5' ends, thereby presenting their 3' hydroxyl groups for reaction, including enzymatic reaction (eg ligation and polymerization). Preferably, this orientation is engineered by preparing nucleotide monomers that bear a phosphoramidite on the 5' oxygen thereof and, on the 3' oxygen thereof, a dimethoxytrityl (DMTr), benzoinyl carbonate (eg a dimethoxybenzoin (DMB) carbonate), MeNPOC, nitrobenzyl carbonate or a styrylsilyl group as described in application Ser. No. 08/339,216 (see also J. Org. Chem. 58:6961 (1993)). Alternatively, an inverse (5' to 3') phosphotriester synthetic approach can be used wherein the monomers are, for example, 3'-O-phosphoryl aryloxybenzoinyl or aryoxynitrobenzyl nucleosides or a 3'-O-phosphorylcyanoethoxy benzoinyl nucleoside. Arrays of the invention have a variety of applications, including detecting mutations in target nucleic acid samples.

Nucleic acid synthesis on a solid support requires: a chemistry for linking the growing chain to the support; a chemistry for effecting internucleotide linkage, including bond formation; and a chemistry for protecting functional groups on the heterocyclic bases. While these chemistries are described herein with reference to DNA synthesis, the approaches used are also applicable to RNA synthesis, with the addition of a protecting group for the 2' hydroxyl of ribose (Narang, "Synthesis and Applications of DNA and RNA", Chapter 5, Academic Press, New York (1987)). Since oligo arrays are used directly, it is important that the oligomers be as pure as possible. One skilled in the art will appreciate that this requires near quantitative yields at every deprotection and coupling step.

Monomers preferred for effecting the 5' to 3' phosphoramidite nucleic acid synthesis of the invention fall into three classes:

a) one to initiate synthesis

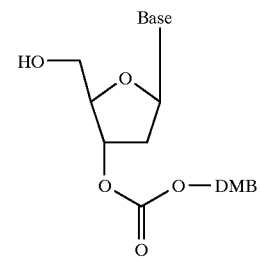

3' DMB carbonate b) one to propagate the growing nucleic acid chain

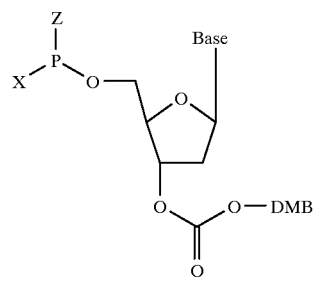

3' DBM carbonate 5'-phosphoramidate c) one to end chain growth

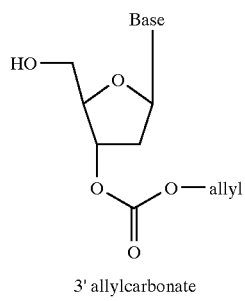

3' allylcarbonate

"Base" in the foregoing structures refers to any of the nitrogenous aromatic heterocyclic substances in nucleic acids eg, adenine, guanine, thymine, cytidine, inosine, uracil, etc. Amino groups, where present on the bases, are protected by groups that can be removed without damaging the DNA backbone or the attachment to the support. Suitable protecting groups include isobutyryl, acetyl, phenoxyacetyl or, preferably, allyloxycarbonyl (AOC) (AOC is readily removed by a catalytic quantity of a palladium complex and a variety of nucleophiles, including butyl ammonium formate or dimedone (Tsuji et al, Acc. Chem. Res. 20:140 (1987)). The sugar to which the base is attached in the above can be ribose, deoxyribose, or modifications thereof, for example, 2'-O-alkylribose or 2' haloribose, eg 2'-fluororibose, "X" in structures (b) and (c) above is $R_2N$ wherein the R's, which can be the same or different, are alkyl or aryl, preferably, $C_1$–$C_4$ alkyl (eg, isopropyl) or phenyl. "Z" in structures (b) and (c) above is O-allyl, O-cyanoethyl or O-chlorophenyl. "Allyl" in structure (c) above is

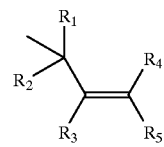

wherein $R_1$=H, alkyl (eg $C_1$–$C_4$ alkyl) or aryl (eg phenyl);

$R_2$=H $R_3$=H, halogen, alkyl (eg $C_1$–$C_4$ alkyl) or aryl (eg phenyl);

$R_4$=H $R_5$=H, halogen, alkyl (eg $C_1$–$C_4$ alkyl) or aryl (eg phenyl).

Preferably, $R_1$–$R_5$ are hydrogen.

An approach to the preparation of the above monomers from AOC-protected bases is provided below:

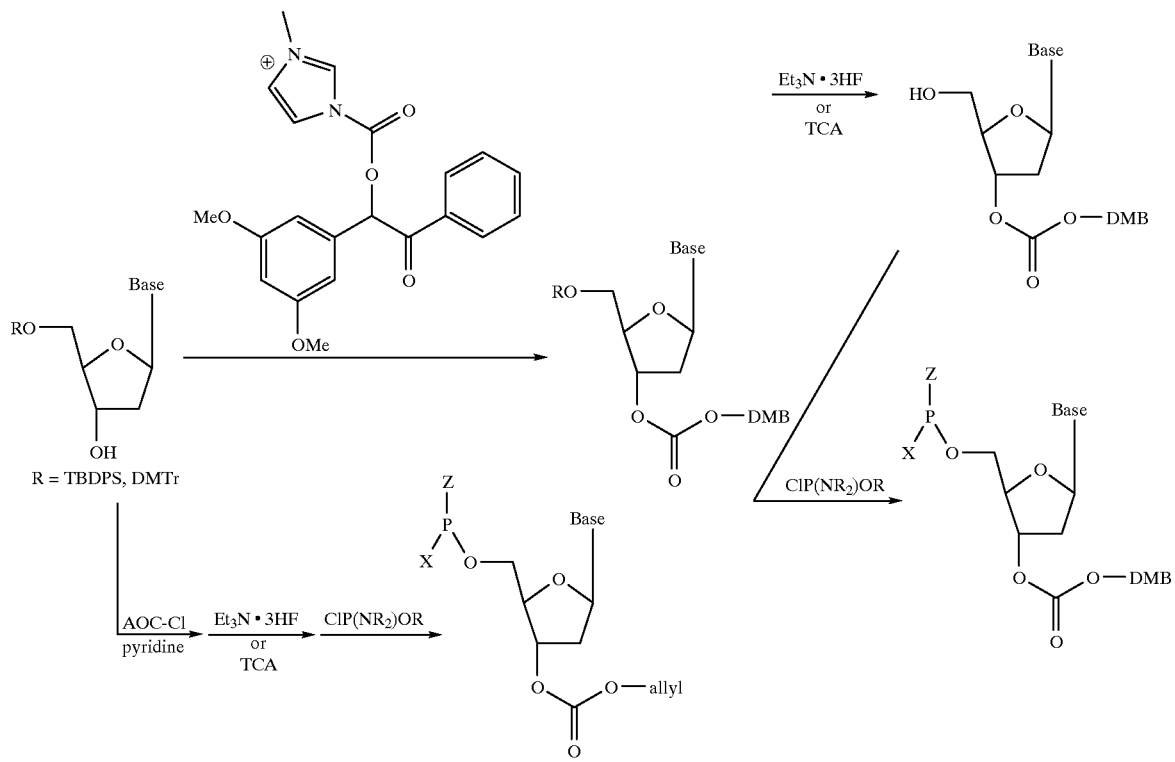

wherein TCA is trichloroacetic acid, TBDPS is tert-butyldiphenylsilyl, DMTr is dimethoxytrityl and AOC-Cl is $CH_2CHCH_2OCOCl$.

Synthesis (5' to 3') using protected species (a), (b) and (c) above can be carried out as follows. A 3'-DMB carbonate ((a) above) is linked through a suitable linker to a support. The support is then irradiated at a wavelength in excess of 300 nm to free the 3' hydroxyl of the support-bound nucleoside. A second nucleotide is added as a 3' DMB carbonate-5'-phosphoramidite ((b) above) and tetrazole-mediated coupling is effected. The resulting phosphite triester is oxidized (eg using t-butylhydroperoxide or $I_2/H_2O$/pyridine) to the phosphate. Unreacted 3' ends are capped, for example, using acetic anhydride/pyridine. Further irradiation results in the presentation of a new 3' end for the next coupling. The process of irradiation, coupling, capping and oxidation is repeated to provide the penultimate sequence. The final nucleotide is added, for example, as the 3' allylcarbonate. The base and internucleotide phosphate protecting groups can be removed simultaneously, with the 3' allyl carbonate, for example, by treatment with a palladium catalyst and butylammonium formate (Hayakawa et al, J. Am. Chem. Soc. 112 1691–1696 (1990)).

When phosphotriester chemistry is used to effect 5' to 3' nucleic acid synthesis, the monomers are protected with 3'-phosphotriesters, one of which is photoremovable. Preferred photoremovable phosphate protecting groups are aryloxybenzoinyl groups, advantageously, dialkoxy benzoinyl groups (eg 3',5' or 2',3'-dimethoxy benzoinyl groups) or a methyl nitropiperonyl group. The 3' phosphotriester can be prepared from 5'-O-DMT base protected nucleosides as described in Example I. During synthesis, protecting groups at the 5' position can be selected, for example, from those known in the art, including TBDPS or DMTr.

By way of example, the synthesis of two dinucleotides (5'-G-T-3' and T-T) can be described as follows. 5'-tert-Butyldiphenylsilyl-N$^7$-allyloxycarbonyl-O$^6$-allyl deoxyguanine-3'-cyanoethyl (dimethoxybenzoin)phosphate (300 mg, 0.295 mmol) is dissolved in 100 ml benzene/1 ml pyridine. The solution is degassed by sparging with Ar and irradiated for 30 min in a Rayonet reactor with 350 nm lamps. The solvent is removed and the residue chromatographed with 90:9:1 $CH_2Cl_2$:EtOH:$Et_3N$ on a column of triethylamine-treated silica to give the product along with a great deal of $Et_3N.HCl$, which is removed by precipitation from ethyl acetate. A single, clean phosphorus line is observed by $^{31}$p NMR and this material is taken to the next step. This dG salt, deoxythymidine-3'-cyanoethyl (dimethoxybenzoin)phosphate (0.278 g 0.443 mmol), and 4-ethoxypyridine N oxide (0.205 g, 1.48 mmol) are azeotroped three times from pyridine and taken up in 12 ml dichloroethane. (Triisopropyl)benzenesulfonylchloride (0.183 g, 0.590 mmol) is added and the mixture is stirred under Ar overnight. TLC reveals three spots, the 5' sulfonate of the T monomer, the desired product, and excess dT monomer. The solvent is removed and the residue chromatographed with 95:5 $CH_2Cl_2$:EtOH on silica gel to give the product (5'-G-T-3', 305 mg, 75%) as a white foam which shows spectra and HRMS (FAB) consistent with the structural assignment. The foregoing procedure can also be applied to 5'-tert-butyldiphenylsilyl-deoxythymidine-3'-cyanoethyl(dimethoxybenzoin)phosphate to give 262 mg (68%) of T-T. The trinucleotide, 5'-G-T-3', can be prepared by dissolving the 5'-G-T-3' dinucleotide (240 mg, 0.175 mmol) in 100 ml benzene/1 ml pyridine and degassing with Ar. Irradiation is performed as above, 1 ml $Et_3N$ is added, and the solvent is removed. This salt, deoxycytidine-3'-cyanoethyl(dimethoxybenzoin)phosphate (0.35 mmol), and 4-ethoxypyridine N-oxide are azeotroped three times from pyridine and then taken up in 10 ml of dichloroethane. (Triisopropyl)benzenesulfonylchloride (106 mg, 0.350 mmol) is added and the mixture is stirred overnight. Chromatography as above provides 219 mg (69%) of 5'-G-T-C-3'.

As indicated above, the present process of nucleic acid synthesis involves linking a first monomer (eg (a) above) to a support (substrate), directly or through a suitable linker. Attachment to the support is through the 5' hydroxyl of the monomer. Suitable supports include long-chain alkylamino controlled pore glass. Substrates described in U.S. Pat. No. 5,143,854 are appropriate for use here, as are the substrate surface treatments described therein. Use of a functionalized glass slide (eg an aminopropylated glass slide) is preferred.

Linker molecules, when used, are dicarboxylic acid derivatives, such as succinic or phthalic esters and amides, or bis adducts of diisocyanates, such as toluene diisocyanate. Succinate is preferred. Linkers referenced in U.S. Pat. No. 5,143,854 are appropriate for use in the present invention. Ethylene glycol oligomers (eg triethylene glycol), succinates (eg diglycine succinate) and tris(aminohexonate) are preferred.

Linkers suitable for use in the present invention are provided with a protective group, that is, a photoremovable group (eg DMB-carbonate, MeNPDC, etc) on a terminal hydroxyl. Protective groups described in U.S. Pat. No. 5,143,854 are applicable here. Preferably, the linker bears a DMB carbonate or DMB phosphate, or photoremovable styrylsilyl group as described in Ser. No. 08/339,216 (see also J. Org. Chem. 58:6961 (1993)).

Attachment of succinate linkers to the substrate can be effected using dicyclohexylcarbodiimide or other carbodiimide. Attachment protocols described in U.S. Pat. No. 5,143,854, for example, can be used.

The 5' to 3' photochemical synthesis of the nucleic acid arrays from the above-described monomers can be effected using straightforward "stripe masking". In general, a support with the appropriate functional group density is treated with a protected nucleoside to affix the first base. The support is then irradiated through a mask (eg a 5 mm striped mask) and coupled with the next base. The process is repeated until an oligomer of desired length (eg 8 to 12 bases) is produced.

Arrays of oligomers prepared, for example, as described above, can be used in detecting mutations in target nucleic acid samples (eg, the p53 tumor suppressor gene). Each array location bearing a primer (oligomer) that is complementary to a site within the target nucleic acid can be used to promote a polymerase catalyzed attachment of one of four detactably-labeled dideoxynucleotides. When fluorescence is used as the detectable label, the color of the fluorescence at each location can identify the nucleotide at the mutation site. Alternatively, the presence of a fluorescent tag can be used to identify array oligomers having sequences complementary to the target. Using this approach, oligomers that do not gain a tag reflect a mismatch within the target due to mutation of the template. Knowledge of the primer sequence at each null location permits determination of the site of mutation.

In addition to the foregoing uses, the methods of the invention and resulting arrays can be used to detect the presence in a sample of a sequence specific, for example, for a bacterial or viral pathogen.

Certain aspects of the present invention are described in greater detail in the non-limiting Examples that follow. Example I relates to 5' to 3' phosphotriester synthesis using 3'-O-phosphoryl aryloxy benzoinyl nucleosides. Example II relates to the preparation and use (as 5' protecting agents) of dimethoxybenzoinyl carbonates and Example III relates to 5' to 3' phosphoramidite synthesis using benzoinyl carbonates as 3'-hydroxyl protecting groups. (See also Pirrung and Shuey, J. Org. Chem. 59:3890 (1994)).

EXAMPLE I

Asymmetric Synthesis of Dimethoxybenzoins, Generation of Phosphotriesters and Dinucleotide Synthesis The methodology used was based on that of Hayashi et al, J. Chem. Soc., Chem. Commun. 1364 (1990). Basically, trimethysilyl cyanohydrins were prepared by treatment of a dimethoxybenzaldehyde with trimethylsilylcyanide, titanium isopropoxide, and diethyl tartrate. The silylcyanohydrins were treated with 2 molar equivalents of phenylmagnesiumbromide in diethyl ether at 0° C. for 1h and hydrolyzed in 2N HCl for 6h at room temperature to yield the substituted benzoin (the alcohol being designated DMBOH). Benzoins so produced were analyzed for optical purity by use of the chiral NMR shift reagent Eu(fod)$_3$. For those compounds that were not optically-pure, crystallization of the racemate was used to raise the enantiomeric excess.

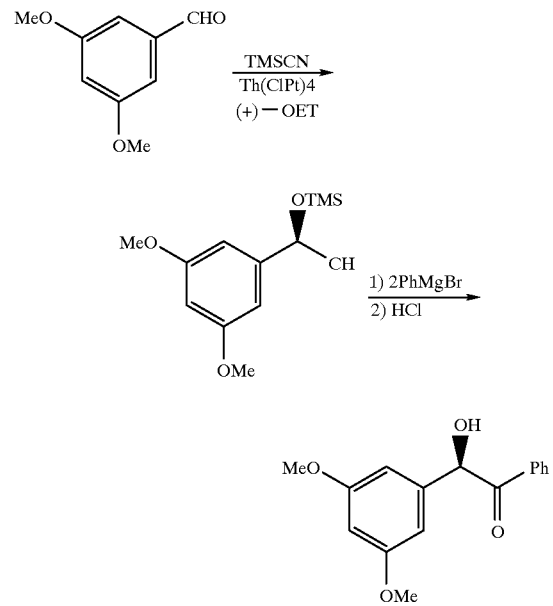

The derivatization of 5'-protected, base-protected nucleosides was conducted as follows. N-Benzoyl-5'-O-acetyl adenosine was treated with Letsinger's reagent, chlorodimethylamino(o-chlorophenyl) phosphite (1.2 eq.) in acetonitrile at room temperature for 2h. The optically active benzoin (1.4 eq.) was added in the presence of a catalytic amount of tetrazole, with coupling proceeding overnight. Oxidation to the phosphotriester was accomplished with a 5% solution of iodine in 1:1 THF/water. The product was isolated by addition of water and chloroform extraction. (See below.) After evaporation of the solvent, the crude product was suspended in methanol and a few drops of triethylamine were added. After 1h at room temperature, the reaction mixture was concentrated and the product crystallized from aqueous ethanol. NMR analysis showed doubling of the signals for the methine in the benzoin group and the 3'-methine in the nucleoside due to the mixture of diastereomers at phosphorous. These could not be separated by any chromotographic or crystallization technique. These compounds are referred to as 3'-O-PArBenz (phosphoryl aryloxy benzoinyl) nucleosides.

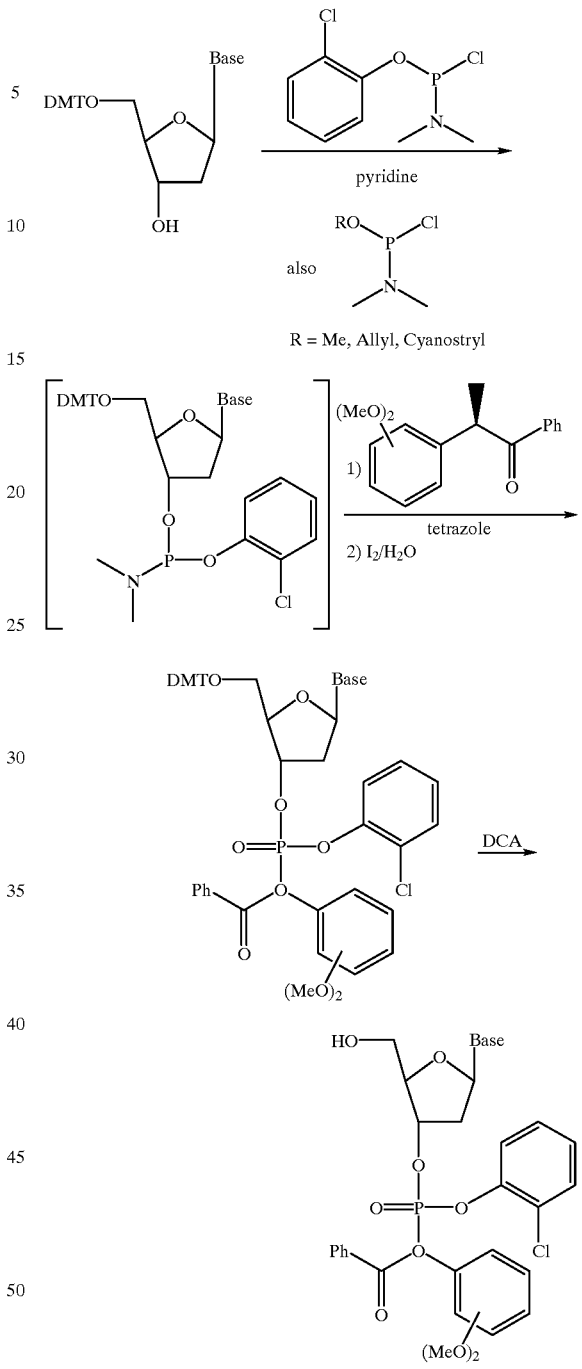

Photochemical synthesis of a dinucleotide was demonstrated by the following experiment. 5'-O-Acetyl-3'-O-PArBenz-thymidine was irradiated at 365 nm in benzene at a power of 10 mW/cm$^2$ for 10 min to produce the 3'-O-phosphate diester. To the solution was directly added N-benzoyladenosine 3'-O-PArBenz (1 eq), mesitylenesulfonylnitrotriazole (MSNT, 1 eq), and pyridine-N-oxide (0.05 eq). After stirring at RT for 2h, the reaction mixture was quenched into water, extracted with chloroform, and the product isolated by evaporation of the combined organic phases. The crude material was then dissolved in methanol/ water (1:1) and 1.1M p-nitrobenzaldehydeoxime/ tetramethylguanidine added. After stirring at 40° C. for 2h, HPLC analysis showed the o-chlorophenyl, acetyl, and benzyl groups were completely removed. The product was isolated in >94% yield by anion exchange chromatography (DEAE-Sephasil), eluting with pH 5.5 triethylammonium bicarbonate.

For the solid phase synthesis of nucleic acids, glass beads or slides are derivatized (functionalized) with 10% dimethyldichlorosilane and hexaethyleneglycol, followed by annealing at 110° C. for 2h and cooling under argon. The support was then treated with Letsinger's reagent at room temperature for 2h followed by a 5'-OH-3'-O-PArBenz nucleoside at room temperature overnight. This procedure attached the first nucleoside to the support via its 5'-hydroxyl group. The support was then irradiated for 10 min at 365 nm at a power of 10 mW/cm$^2$ in contact with a solution containing triethylamine and p-diethylaminonitrobenzene (the irradiation time for the production of the phosphodiester for coupling is important, 6 min was found to be optimum). If the support is a slide, the irradiation can be conducted through a mask to impose a pattern on the surface. The support is washed with pure methylene chloride. A solution of a 5'-OH-3'-O-PArBenz nucleoside and mesitylenesulfonyl nitrotriazole (MSNT) (0.1 M solution in DMF) is then added to the support and allowed to stand for 2h at RT. The support is again washed with methylene chloride in preparation for the next irradiation cycle. At this stage, a dinucleotide is present bearing a 3'-O-PArBenz group, and the foregoing procedure can be repeated to build up the desired sequence. After the complete sequence is assembled, a final irradiation removes the 3'-photolabile group and treatment as described earlier with nitrobenzaldehydroxime deprotects the support-bound oligonucleotide.

The sequence of this nucleotide was established in two ways. Supports containing only one sequence were treated with aqueous potassium fluoride to liberate all DNA chains. The DNA was ethanol precipitated and subjected to FAB mass spectrometry. These DNA molecules can also be used as PCR primers, and by comparison to known quantities of the same sequence made and purified by conventional methods, an estimate of the quantity of the desired sequence, and therefore the purity of the obtained sequence, was made.

The yield of a synthesis cycle on the support was established by coupling a hydroxyl surface with thymine bearing a 3'-PArBenz group. It was deprotected in a stripe and coupled with a 3'-acetyl thymine. The acetyl group was removed with MeOH/Et$_3$N and the 3'-hydroxyl fluoresceinated. The substrate was photochemically deprotected in a second stripe overlapping and orthogonal with the first and the 3'-hydroxyls were fluoresceinated. Provided deprotection and coupling are complete in both steps, the result of this experiment should be a cross of uniform fluorescence throughout.

If deprotection is not complete, the center region should be more fluorescent because it was "double-coupled".

EXAMPLE II

Dimethoxybenzoin Carbonates

Carbonyliimidazole activated by methylation (Saha et al, J. Am. Chem. Soc. 111:4856 (1989)) in nitromethane performed a single acylation of DMB (1 hr RT) to provide "1" below which was stable even at reflux temperatures (eq 1 below). Addition of a solution of alcohol (0.5 eq) followed by pyridine leads to acyl substitution to generate the DMB carbonate within 1 h at RT (eq 2 below). Primary, secondary, and aryl alcohols and thiols (including benzyl alcohol, benzylmercaptan, pmethoxyphenol, cholesterol, cyclododecanol and borneol) have been protected in high yield. These compounds were readily deprotected on irradiation with 350 nm lamps (Rayonet reactor) as dilute (≦3mM) solutions in benzene or acetonitrile. Typical reaction times were 1 h on a 0.25 mmol scale (2x longer in acetonitrile), and the isolated yields of the alcohols were uniformly high (>96%). Parallel irradiations of DMB acetate and benzyl DMB carbonate at low concentration show essentially the same rate of deprotection suggesting the quantum yield of deprotection for these carbonates is similar to that reported for the acetate, 0.64. A significant advantage of these benzoin groups compared to nitrobenzyls is the inert phenyldimethoxybenzofuran byproduct. Its long wavelength (300 nm) absorbance and intense 396 nm fluorescence permit its detection at concentrations as low as 1 μM, permitting the yield of a photochemical deprotection to be directly measured by optical methods.

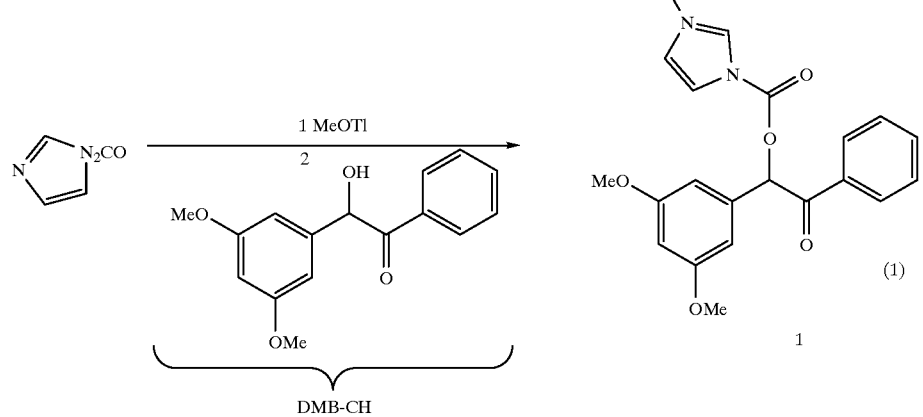

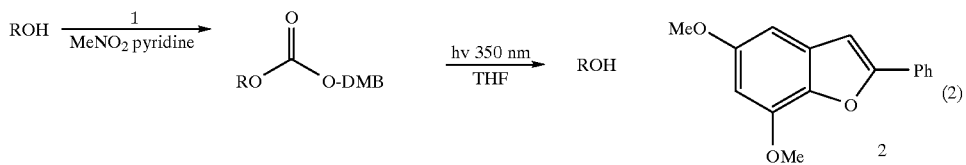

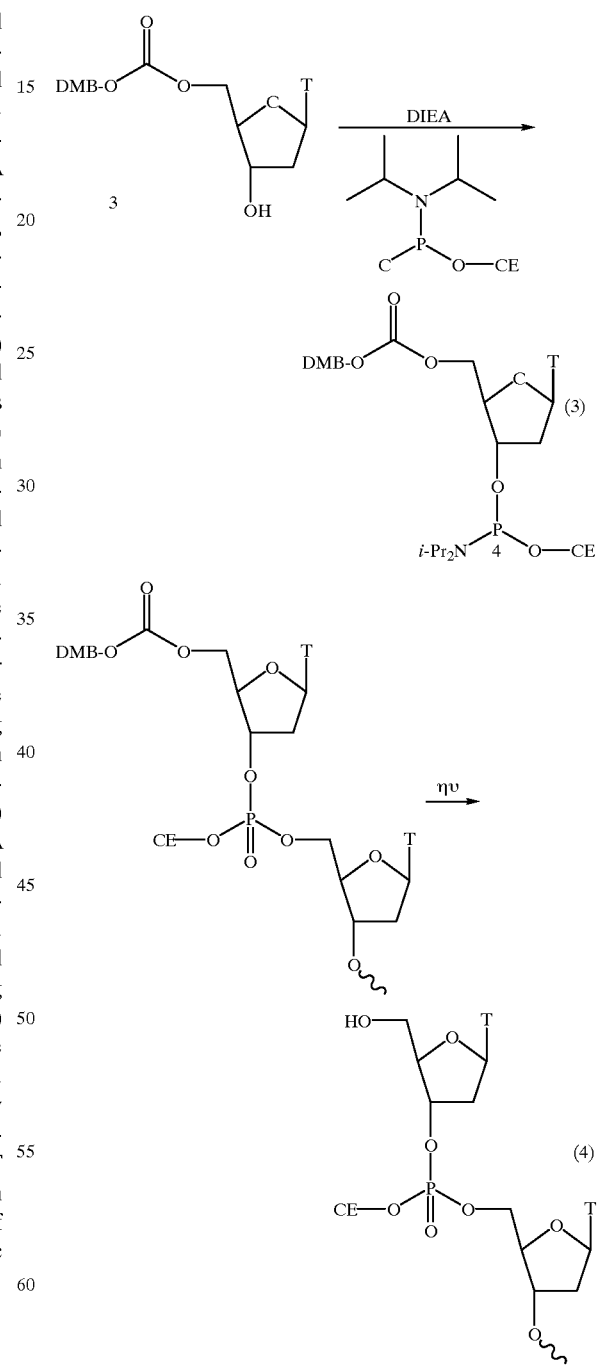

To demonstrate the utility of the DMB carbonate protecting group for the photochemical synthesis of DNA on solid support, two trimers were prepared. Derivatization of thymidine at the 5' alcohol with the DMB-carbonate and conversion of the resulting "3" below to the 3'-phosphoramidite "4" below was accomplished by standard methods (eq 3 (Gait "Oligonucleotide Synthesis: A Practical Approach" IRL Press Oxford 1984; Narang, "Synthesis and Applications of DNA and RNA" Academic Press, New York (1987); Gassen and Lang, "Chemical and Enzymatic Synthesis of Gene Fragments" Verlag-Chemie, Weinheim (1982); Caruthers, Science 230:281 (1985)). Commercial long-chain alkylamine controlled-pore glass (lcaa-cpg) beads derivatized with 5'-DMTr-T (25 μmol/g) were treated with acid and coupled to "4" below under tetrazole catalysis with acetic anhydride/dimethylamino pyridine (DMAP) capping. Irradiation (eq 4 below) and coupling with 5'-DMTr-Bz-cytosine 3'-CE-phosphoramidite gave a trinucleotide. The protecting groups and tether were cleaved with ammonia and the product subjected to HPLC purification (reverse phase, 0.1 M $Et_3N \cdot HOAc$/24–32% $CH_3CN$). The absorbance of the fraction containing the sequence 5'-DMTr-CTT was compared to that of a known concentration of an authentic sample (prepared by conventional DMTr synthesis) to determine an overall yield of 76.5%. The sequence 5'-ATT-3' was prepared by first loading a lcaa-cpg support with 5'-DMB-$CO_2$-T (184 nmol by benzofuran release) through its 3' succinate by dicyclohexylcarbodiimide treatment. Irradiation ($t\frac{1}{2}$=2.7 min; total time=30 min) and coupling with "4" below was conducted as above. A second irradiation ($t\frac{1}{2}$=3.3 min, total time =45 min) and coupling (167 nmol by benzofuran release) with 5'-DMTr-Bz-adenosine 3'-CE-phosphoramidite gave a trinucleotide. It was cleaved from the support, analyzed by HPLC and showed a single peak. This product was also purified using an OPC cartridge (Applied Biosystems, Foster City, Calif.) and digested with snake venom phosphodiesterase/alkaline phosphatase (Cadet et al, Can. J. Chem. 63:2861 (1985)). The nucleosides in the resulting sample were analyzed by HPLC. A ratio of 64.5%/35.5% (T/A) was observed, consistent with the expected sequence. Despite the adjacent T residues in these two sequences, photochemical deprotection is not injurious to the DNA, as established by the absence of any T-T dimer product by comparison to an authentic sample. (Greenberg et al, J. Org. Chem. 59:746 (1994)).

Secondary dimers have also been protected with "1" above and deprotected on irradiation.

EXAMPLE III

Protection of the 3' Alcohol of a Nucleoside with a Photoremovable Carbonate Derivative, Protection of the 5' Alcohol with a Phosphoramidite, and Coupling of 5'-Phosphorous Derivative with a 3'-Alcohol Carbonyldiimidazole is treated with methyl triflate in nitromethane to generate the N-alkyl imidazolium derivative (see Example II above). Treatment of this species in situ with 3',5'-dimethoxybenzoin generates a mixed carbonate ester/imidazole. A 5'-protected nucleoside is then added and the solution refluxed for 2 hr to generate the mixed carbonate from DMB and the 3' hydroxyl of the nucloside. This material can be deprotected at the 5' end and further derivatized on the 5'-hydroxyl with a phosphoramidite reagent (Caruthers, Science 230:281 (1985)). Coupling of this 5'-phosphorous derivative with a 3'-alcohol of a second nucleoside is accomplished with a tetrazole catalyst. The nascent DNA chain is prepared for another coupling cycle by irradiation with light of a wavelength of >300 nm which generates a benzofuran derivative, carbon dioxide and the free 3'—OH group. The foregoing can be used to effect protection of other alcohols, includuing the 5' alcohol of a nucleoside (see Example II). Thiol protection can also be carried out as described above.

All documents cited above are hereby incorporated in their entirety by reference.

One skilled in the art will appreciate from a reading of this disclosure that various changes in form and detail can be made without departing from the true scope of the invention.

What is claimed is:

1. A method of effecting 5' to 3' synthesis of a nucleic acid comprising:
   i) attaching to a support a nucleoside comprising a photoremovable 3' hydroxyl protecting group, wherein said attachment is via the 5' hydroxyl of said nucleoside;
   ii) irradiating said support-bound nucleoside resulting from step (i) so that said protecting group is removed and said 3' hydroxyl group is thereby freed; and
   iii) contacting the support-bound nucleoside resulting from step (ii) with nucleoside a 5' phosphoramidite under conditions such that said 5' phosphoramidite reacts with the free 3' hydroxyl so that a dinucleotide is formed.

2. A method of effecting 5' to 3' synthesis of a nucleic acid comprising:
   i) attaching to a support a nucleoside having a photoremovable 3' hydroxyl protecting group, wherein the 3' hydroxyl protecting group is a benoinyl carbonate and wherein said attachment is via the 5' hydroxyl of said nucleoside;
   ii) irradiating said support-bound nucleoside resulting from step (i) so that said protecting group is removed and said 3' hydroxyl group is thereby freed; and
   iii) contacting the support-bound nucleoside resulting from step (ii) with a nucleotide having a 5' phosphoramidite under conditions such that said 5' phosphoramidite reacts with the free 3' hydroxyl so that a dinucleotide is formed.

3. The method according to claim 2 wherein said benzoinyl carbonate is a dialkoxy benzoinyl carbonate.

4. The method according to claim 3 wherein the dialkoxy benozionyl carbonate is 3',5' or 2',3' dimethoxy benzoinyl carbonate.

5. The method according to claim 1 wherein said nucleotide has a 3' hydroxyl protecting group.

6. The method according to claim 5 wherein said 3' hydroxyl protecting group of said nucleotide is photoremovable.

7. A nucleotide having a phosphoramidite on the 5' hydroxyl thereof and a benzoinyl carbonate on the 3' hydroxyl thereof.

8. A compound of formula

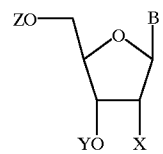

wherein: B is a nitrogenous aromatic heterocyclic group;

X is H, OH or a protected OH;

Y is a benzoinyl carbonate; and

Z is a phosphoramidite.

9. The compound according to claim 8 wherein Y is a dialkoxybenzoinyl carbonate.

10. The compound according to claim 9 wherein Y is di($C_1$–$C_4$)alkoxybenzoinyl carbonate.

11. The compound according to claim 10 wherein Y is 3',5' or 2',3' dimethoxybenzoinyl carbonate.

12. The compound according to claim 8 wherein B is uracil, adenine, guanine, thymine, cytosine or inosine.

13. A method of effecting 5' to 3' synthesis of a nucleic acid comprising:
   i) attaching to a support a nucleoside having a photoremovable 3' hydroxyl protecting group, wherein said attachment is via the 5' hydroxyl of said nucleoside;
   ii) irradiating said support-bound nucleoside resulting from step (i) so that said protecting group is removed and said 3' hydroxyl group is thereby freed; and
   iii) contacting the support-bound nucleoside resulting from step (ii) with a nucleotide having a photoremovable 3' hydroxyl benzionyl carbonate protecting group and a 5' phosphoramidite under conditions such that said 5' phosphoramidite reacts with said freed 3' hydroxyl so that a dinucleotide is formed.

14. The method according to claim 2 wherein said nucleotide comprises a photoremovable 3' hydroxyl protecting group.

15. The method according to claim 14 wherein said 3' hydroxyl protecting groups is a benzionyl carbonate.

16. The method according to claim 14 further comprising the step of irradiating said dinucleotide resulting from step (iii) so that said 3' hydroxyl protecting group of said nucleotide is removed and said 3' hydroxyl group of said dinucleotide is thereby freed.

17. The method according to claim 13 further comprising the step of irradiating the dinucleotide resulting from step (iii) that so that said 3' hydroxyl group of said dinucleotide is thereby freed.

18. The method according to claim 1 further comprising enzymatically extending said nucleic acid.

19. The method according to claim 2 further comprising enzymatically extending said nucleic acid.

20. The method according to claim 13 further comprising enzymatically extending said nucleic acid.

* * * * *